United States Patent [19]
Iwaki

[11] Patent Number: 6,050,387
[45] Date of Patent: Apr. 18, 2000

[54] DEVICE AND METHOD FOR IDENTIFYING BANK NOTE

[75] Inventor: Kunihide Iwaki, Yokohama, Japan

[73] Assignee: Yokohama Denshi Kogyo Kabushiki Kaisha, Kanagawa-ken, Japan

[21] Appl. No.: 09/033,967

[22] Filed: Mar. 3, 1998

[30] Foreign Application Priority Data

Sep. 10, 1997 [JP] Japan ..................... 9-245683

[51] Int. Cl.[7] .............. G06K 7/00; G06K 9/00; G01J 1/32
[52] U.S. Cl. ............ 194/207; 382/135; 250/205; 356/71
[58] Field of Search ............ 194/207; 382/135; 250/205, 556; 356/71

[56] References Cited

U.S. PATENT DOCUMENTS

| | | | |
|---|---|---|---|
| 4,352,559 | 10/1982 | Gorgone et al. | 250/556 |
| 4,587,434 | 5/1986 | Roes et al. | 356/71 |
| 4,769,532 | 9/1988 | Kawakami | 382/135 |
| 5,476,169 | 12/1995 | Takarada et al. | 194/207 |

FOREIGN PATENT DOCUMENTS

| | | | |
|---|---|---|---|
| 54-29397 | 9/1979 | Japan . | |
| 58-9478 | 1/1983 | Japan . | |
| 59-2188 | 1/1984 | Japan . | |
| 62-111377 | 5/1987 | Japan . | |
| 2-71395 | 3/1990 | Japan . | |
| 3-14195 | 1/1991 | Japan | 194/207 |
| 4-134583 | 5/1992 | Japan | 194/207 |

OTHER PUBLICATIONS

Nakano and Kuwano; "Color Sensors and Their Application Techniques"; Sensor Interfading No. 2; 1983; pp. 73–80.
Kishi and Inoue; "Color Sensor for Video Camera and Its Applications"; Sensor Gijyutsu; 1988; vol. 8, No. 7, p. 59.
Takashima; "FA Coating Quality Control/Control System"; Sensor Gijyutsu; 1988; vol. 8, No. 7, p. 64.
Nishihara and Tokumaru; "Full Color Mark Sensor"; Sensor Gijyutsu; 1991; vol. 11, No. 4, p. 67.

*Primary Examiner*—Robert P. Olszewski
*Assistant Examiner*—Bryan Jaketic
*Attorney, Agent, or Firm*—Merchant & Gould P.C.

[57] ABSTRACT

A device and method for identifying a bank note with simple construction offering easy adjustment and a reliable performance independent of the environment under which it works. The device enables identification of a bank note printed in color with a genuine one by the method of adjusting the intensity of light emission so as to equalize sensitivity of a photoelectric transducer to a light source A and a light source B, emitting lights in different wavelengths when there is no object to be identified, detecting the difference in sensitivity of detected signals of light transmitted through or reflected by the object to be identified as output of a high-pass filter, and sampling, in a sampling circuit, a signal based on the sensitivity difference and proportional to the difference between detected value for light source A and sensitivity of light source B to conduct identification based on the sampling value.

9 Claims, 8 Drawing Sheets

DEVICE AND METHOD FOR IDENTIFYING BANK NOTE

BACKGROUND OF THE INVENTION

1. Field of the Invention

The present invention relates to a device and method for identifying a security or bank note (hereinafter bank note) which can easily separate a genuine bank note from a false one.

2. Description of the Related Art

Recently, use of various types of vending machines has rapidly proliferated handling all sorts of merchandise. Certain types of vending machines have been introduced which can handle not only coins but also bank notes. Since vending machines are set up in various locations and undergo diversified operational conditions, they are required to be able to perform satisfactorily under all sorts of operational environments. This also applies to mechanisms for distinguishing genuine coins and/or bank notes from false ones.

A mechanism for identifying genuine coins can be constructed by a mechanical system, as false coins can be separated from genuine ones by checking their weights and/or shapes.

On the other hand, it has been almost impossible to recognize a bank note as genuine or false by a mechanical system. Rather, identification has been conducted by optically checking the extent of light transmission through a bank note. In a conventional way of bank note identification a light source and a light receiving element are positioned with specified distance between them to transport a bank note therebetween for detecting a bright-dark pattern peculiar with regard to the light source to compare with a reference bright-dark pattern stored in advance for determination of genuine or false.

However, in such a case, there existed a likelihood of easily mistaking a copy of a bank note as a genuine one, since identification of genuine or false has been done only by means of a bright-dark pattern.

Use of a color sensor may be proposed to improve this point but it is impossible to use such an expensive device as a color sensor, which requires complicated signal processing for a vending machine for which low production cost is an essential factor.

Further, it is required to use an incandescent light source (incandescent bulb) but an incandescent light source tends to be short lived and especially when a vending machine is set up on a roadside under hot summer sun, it is exposed to strong light and heat which causes a breakdown of a bulb in a short while. In such a case even a genuine bank note is mistaken as false when it is inserted into such a vending machine making it useless.

To solve those disadvantages, it may be proposed to determine color tint of a bank note by employing, for example, 2 light emitting diodes (LED), which emit lights in different wavelengths as light sources and a light receiving element which receives light emitted from each of the LEDs. However, as LEDs have diversified light emission characteristics, it was necessary to adjust set-up positions and drive currents of LEDs to obtain a uniform performance ratio between 2 LEDs.

Further, in case of a vending machine which is supposed to be set up in the outdoors, it is difficult to maintain a constant ratio of intensity of light emitted by LEDs. This totally applies to a light receiving element. This resulted in unreliable performance of a bank note identification device and it was not suitable for actual usage. To solve such disadvantages, disclosed in Japanese Examined Patent Publication No. 58-9478 is a device which is provided with 2 LEDs, one of them being green, while the other is red, lights emitted from the 2 LEDs being received by a light receiving element and the quantity of light emitted by the 2 LEDs being controlled so as to be equal, when there is no bank note between the LEDs and a light receiving element. When a bank note comes between the LEDs and the light receiving element, an error signal is to be generated, either if an output of the light receiving element derived from the light of green LED takes a higher value than a reference level indicating the color of the bank note is inclined toward green in certain degrees or if the output of the light receiving element derived from the light of the red LED takes a higher value than the reference level, indicating the color of the bank note is inclined toward red in certain degrees.

However, the device in Japanese Examined Patent Publication No. 58-9478 is based on a premise that when the color of a bank note is not inclined (not shifted) toward red or green, the quantity of light received by the light receiving element put its output at zero level, which is totally equal to the output level found when there is no bank note. It can only generate an error signal in identifying such a bank note, when the color of a bank note is shifted toward green or red in certain degrees and it can be expected to have some effect only for a bank note printed in certain colors but it was almost impossible to identify bank notes printed in many colors such as Japanese paper money.

For example, it can not generate an error signal when a bank note is printed or copied in monochrome, making it useless under actual circumstances.

SUMMARY OF THE INVENTION

It is an object of the present invention to provide a device and method for solving the aforementioned problems. It is another object of the present invention to provide a device and method for identifying a bank note which is highly reliable and easily manufactured and adjustable and capable to automatically solve problems such as variation of performance of each component of the detection mechanism of the identification device, change due to aging and change in performance due to surrounding environment with simple construction.

To attain such objects the present invention provides a device and method for identifying a bank note comprising first light emitting means for emitting light in a specified wavelength, second light emitting means emitting light in a wavelength different from that of the first light emitting means, first drive means for driving the first light emitting means to emit light, second drive means for driving the second light emitting means to emit light, light emission control means for activating the first and second drive means by sequentially switching them, light receiving means for outputting electrical signals corresponding with detected light intensity by receiving both of the lights emitted from the first and second light emitting means, adjustment means for adjusting the intensity of the light emission by adjusting at least one of the first and second drive means so as to keep the difference in the level between electric signals generated in the light receiving means corresponding with the lights with different wavelengths from each of the light emitting means within a specified range to eliminate variations in performance of each light emitting means and the light receiving means, means for fixing light intensity to fix the adjusted state of the adjusting means when an object to be identified reaches between both of the light emitting means and the light receiving means, extracting means for extracting an alternating current component of the electrical output signals from the light receiving means during transportation of the object to be identified between the light emitting means and the light receiving means, and sampling means for sampling alternating current output signal value in the alternating current output signal from the extracting means at the time of receiving light from either one of the light emitting means, whereby identification of a bank note is conducted based on the sampling value from the sampling means.

Further, for example, the invention is characterized to conduct identification of a bank note by checking the extent of similarity between a sampling value derived in the sampling means and the value of a genuine object to be identified stored in advance. Or else, in another embodiment, the invention is characterized by constructing the first and second light emitting means with LEDs, arranging both of the LEDs and the light receiving means opposedly facing each other, the object to be identified being transported between the first and second LEDs and the light receiving means, while an optical filter may be disposed between the first and second LEDs and the light receiving means.

In another example, the invention is characterized by constructing the first and second light emitting means with LEDs, disposing the light receiving means between the first and the second LEDs so as to be able to receive lights emitted from both of the LEDs after they are reflected from a reference reflector, while an object to be identified is transported between the first LED, second LED, the light receiving means and the reference reflector.

These and other objects and features of the present invention will be apparent by referring to the following detailed description of the embodiments of the invention, taken together with the accompanying drawings.

DETAILED DESCRIPTION OF THE PREFERRED EMBODIMENTS

Figure 1:
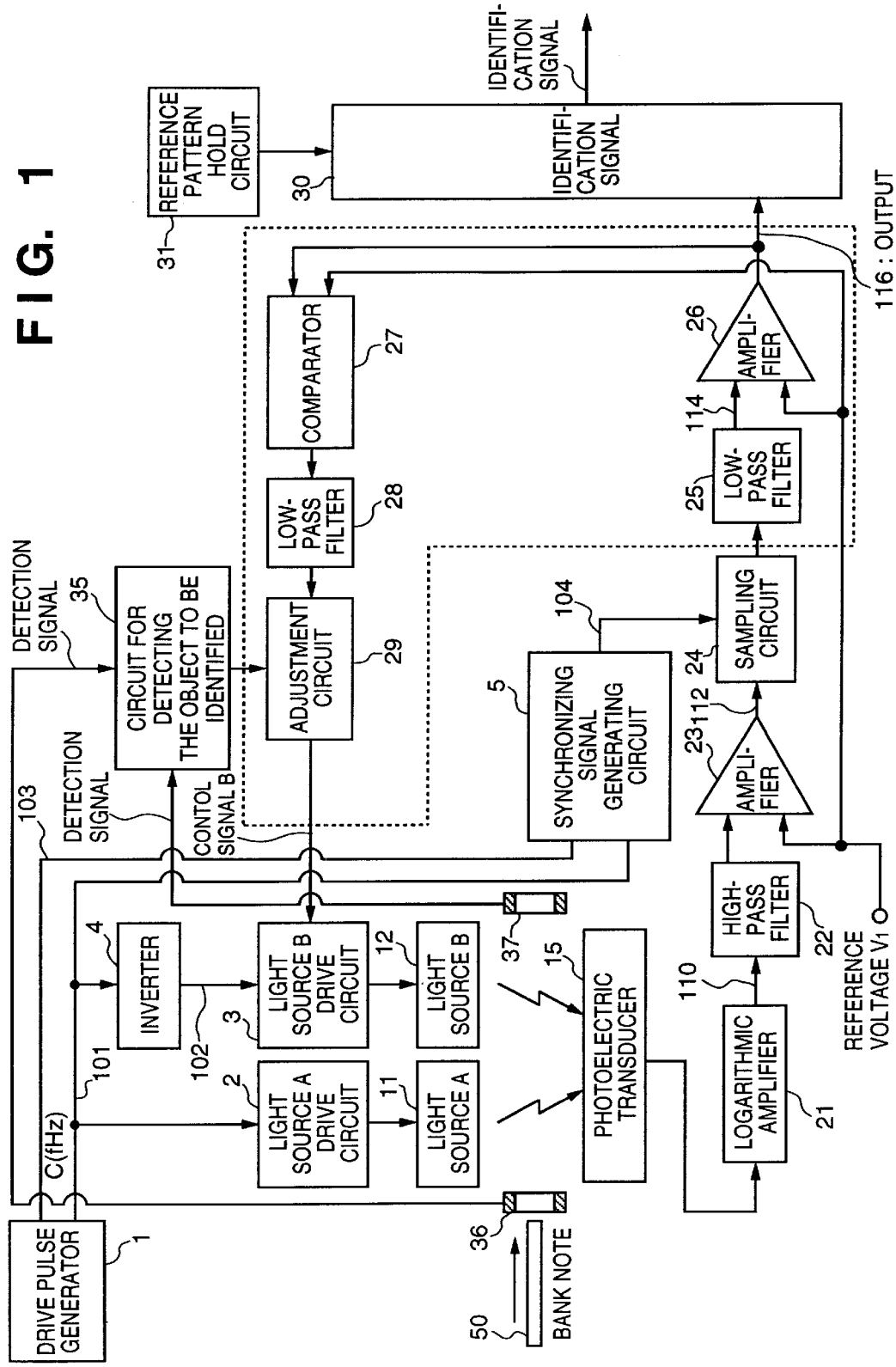
FIG. 1 is a block diagram illustrating construction of a device for identifying bank note according to an embodiment of the present invention.

Now referring to the drawings, an embodiment of the invention will be described in more details.

First Embodiment

Figure 2:
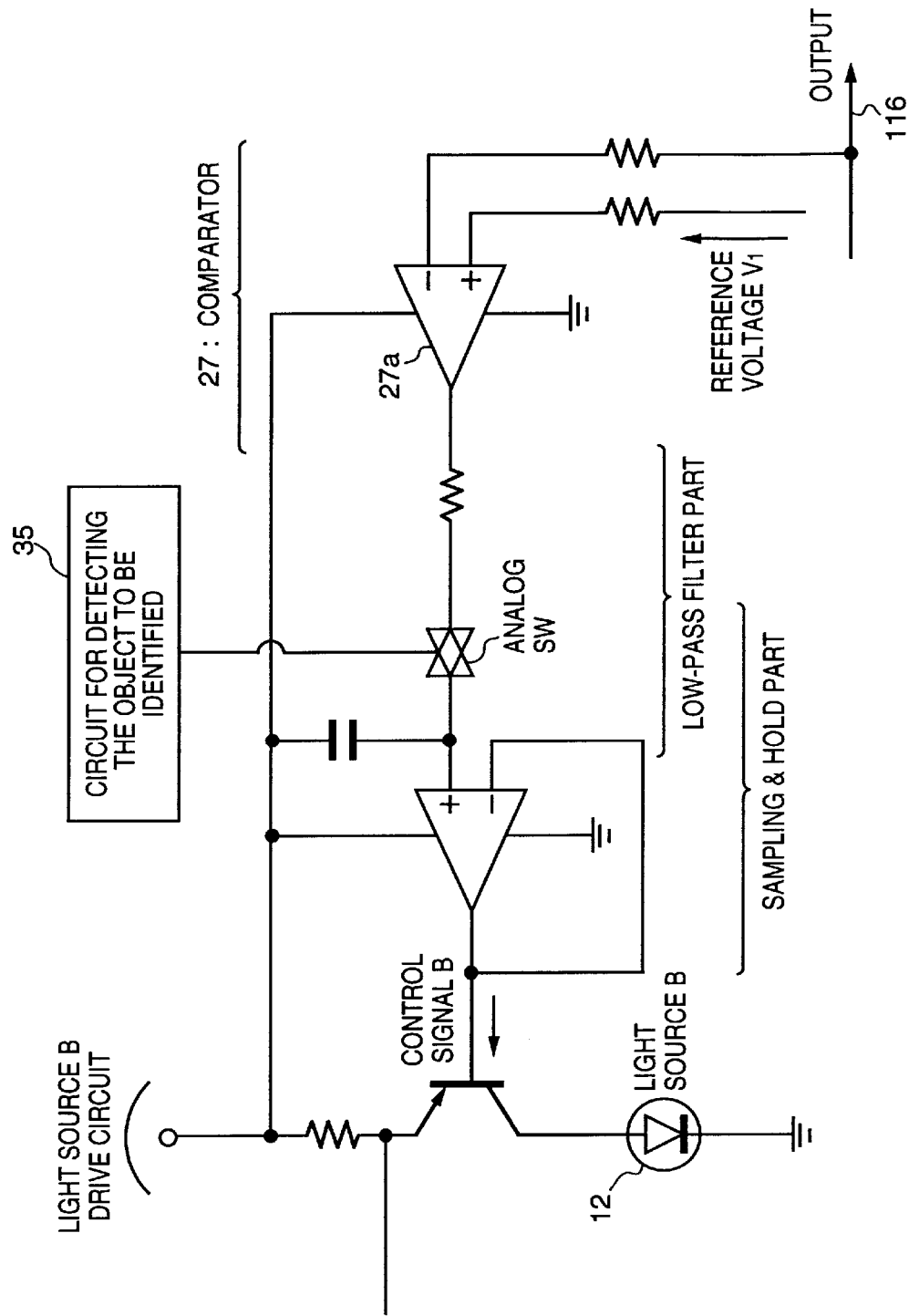
FIG. 2 is a block diagram illustrating detailed construction of the circuit for automatically adjusting intensity of light emission from light sources shown in FIG. 1
Figure 3A:
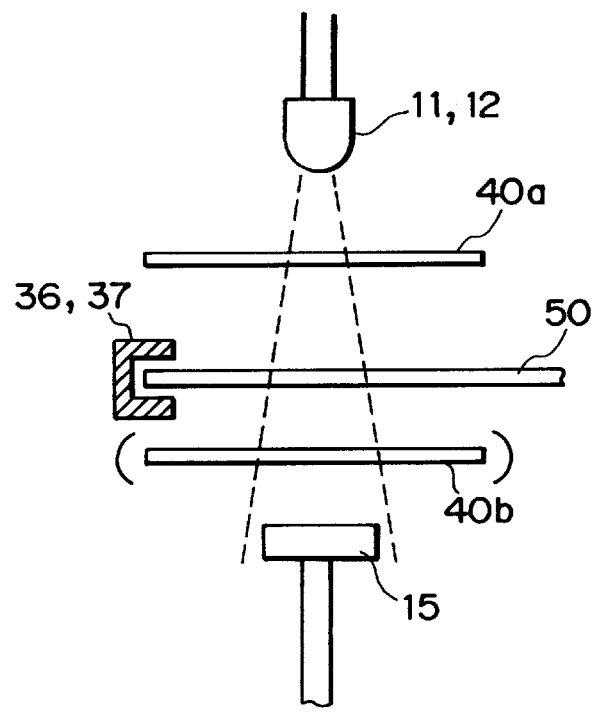
FIGS. 3A and 3B are drawings illustrating arrangement of the light emitting elements and the light receiving element in an embodiment of the present invention.
Figure 3B:
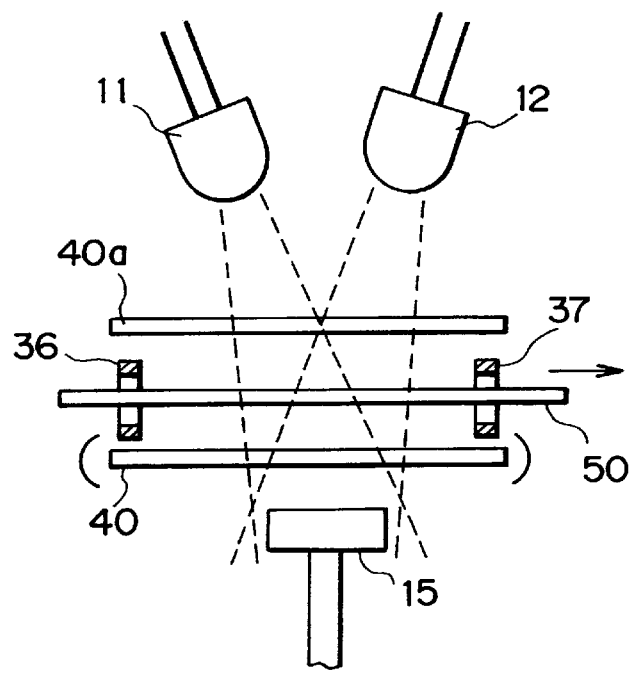
Figure 4:
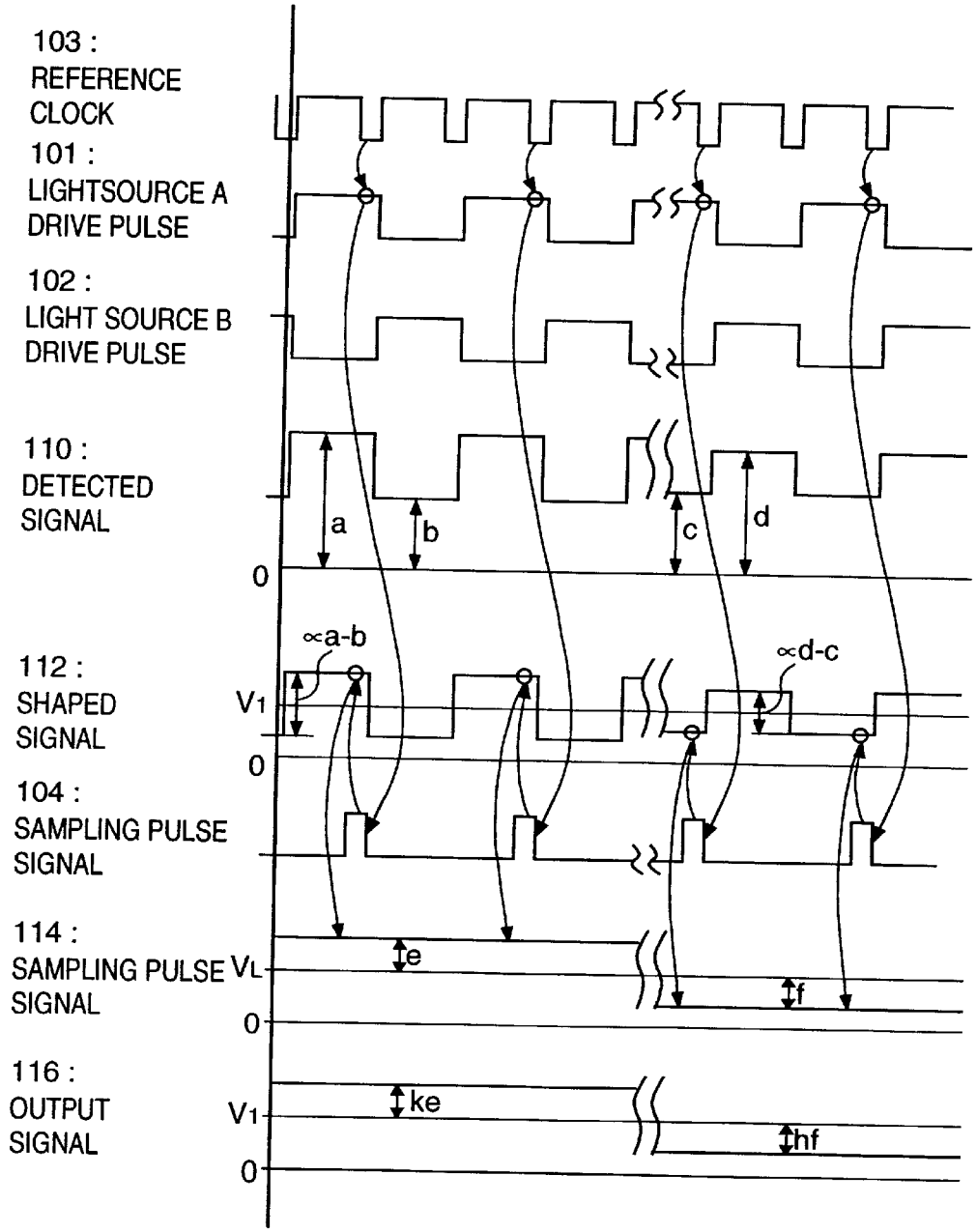
FIG. 4 is a time chart for explaining the operation of the embodiment shown in FIG. 1 of the present invention.

FIG. 1 is a block diagram illustrating construction of a device for identifying bank notes according to an embodiment of the present invention. FIG. 2 is a block diagram illustrating detailed construction of the circuit for automatically adjusting the intensity of light emission from light sources shown in FIG. 1. FIGS. 3A and 3B are drawings illustrating the arrangement of the light emitting elements and the light receiving element in an embodiment of the present invention and FIG. 4 is a time chart for explaining the operation of the embodiment shown in FIG. 1 of the present invention.

In FIG. 1, a drive pulse generator 1 for generating reference drive pulses of this embodiment generates and outputs a reference clock signal 103 (frequency 2f) along with light source A drive pulse 101 (frequency f) which is obtained by dividing the reference clock signal 103. In this embodiment the pulse frequency f is set at 4 KHz.

A light source A drive circuit 2 controls emission of light from the light source A 11. A light source B drive circuit 3 controls emission of light from the light source B 12. The light source B drive circuit 3 controls the quantity of light emission from the light source B 12 in response to control signal B from an adjustment circuit 29. An inverter circuit 4 generates light source B drive pulse 102 by reversing light source A drive pulse 101.

A synchronizing signal generating circuit 5 generates sampling pulses 104 from reversed signals of the reference clock 103 and light source A drive pulse 101 and then feed them into a sampling circuit 24.

A light source A 11 is, for example, a red LED emitting red light and a light source B 12 is a LED emitting light in a different wavelength from light source A, for example, in green. As shown in FIG. 4, the light source A 11 and light source B 12 are driven to emit lights by oppositely phased drive pulses 101 and 102, respectively, and are controlled to emit lights in an alternate sequence.

A photoelectric transducer 15 receives lights emitted from the light source A 11 and the light source B 12 to convert them to output electric signals corresponding to the quantity of received lights and may consist of, for example, a photo diode. A logarithmic amplifier 21 amplifies electric signals from the photoelectric tansducer 15.

In this embodiment of the present invention, the value of received light signal (value of signal for detecting the ratio of light intensity of the light source 11 to that of the light source 12) from the photoelectric transducer 15 is amplified by a logarithmic amplifier 21, because, if a linear amplifier is used, it is basically impossible to eliminate shifts related to such absolute value components of light emission intensity as deviations in distance between a light source and a photoelectric transducer, intensity of emitted light and sensitivity to received light or temperature characteristics and deterioration, as absolute value components of intensity of emitted lights essentially come out in the output of the linear amplifier when an object to be identified is inserted between the light sources A 11 and B 12 and photoelectric transducer 15, while if a logarithmic amplifier is used, it is possible to obtain output via line 110 only related to the property of an object to be identified. Moreover, a method is adopted in which difference of outputs of the same logarithmic amplifier is taken, because it allows elimination of the need for Is cancellation intrinsic to a logarithmic amplifier, which enables simplification of the design of the logarithmic amplifier itself.

Namely, if a linear amplifier is used, $$V(Ma+N)-(Mb+N)=Ma-Mb$$

where, V is the wave height value, Ma the light intensity of the source A 11, Mb that of the source B 12, common steady-state background N.

If a logarithmic amplifier is used, $$V \ln(Ma+N) - \ln(Mb+N) = \ln\{(Ma+N)/(Ma+Mb)\}$$

When automatic adjustment is implemented so as to make the value of the wave height to be 0, if a linear amplifier is used, $$Ma - Mb = 0 \therefore Ma = Mb$$

while, a logarithmic amplifier is used, $$(Ma+N)/(Mb+N) = 1 \therefore Ma = Mb$$

Consequently, both cases result in the same light emission condition.

However, under the above condition Ma=Mb ($\equiv$C), if an object to be identified with light transmittances (or reflectances) a and b for the lights from the sources 11 and 12, respectively, is inserted between the sources A 11 and B 12 and photoelectric transducer 15, the wave height value V is, for a linear amplifier, $$V \ aMa - bMb = (a-b)C$$

which shows that an absolute value component C in intensity of light emission appears in the output, while for a logarithmic amplifier, $$V \ln\{(aC+N)/(bC+N)\}$$

which can be expressed approximately as, $$V \ln\{(aC)/(bC)\} = \ln(a/b)$$

under a condition aC, bC>>N (N may be a non-steady state), which enables obtaining only property of the object to be identified, even though with some conditions. This is a reason why a logarithmic amplified is used in the individual embodiment of the present invention.

A high-pass filter 22 eliminates components less than f (direct current component and fluctuation related to brightness produced between direct current and f) in the detected electric signal from the logarithmic amplifier 21 to extract alternating current components synchronized with the drive pulses 101 and 102.

An amplifier 23 superposes the reference direct current V1 over output of the high-pass filter 22 for output. A sampling circuit 24 samples the output signals via line 112 from the amplifier 23 by means of sampling pulse 104 from synchronized signal generating circuit 5 to hold and output the sampled value.

In this embodiment of the present invention, the sampling pulse from the synchronized signal generating circuit 5 is outputted in synchronization with the timing of emitted light reception from the source A 11 to obtain output corresponding to difference of quantity of received light from both of the sources A 11 and B 12.

A low-pass filter 25 eliminates the frequency (f) component and its harmonic components in the drive pulses 102 and 103 from output signal of the sampling circuit 24. An amplifier 26 amplifies the output via line 114 from the low-pass filter 25 in a specified ratio with reference to the reference voltage V1 to output signal amplified by amplification factor k of the amplifier 26. By the way, at the time of the automatic adjustment of quantity of light from the light source (at the time of negative feed-back) its output becomes as V1.

In this embodiment of the present invention, a circuit for automatic adjustment of the intensity of light emission from the light source which is shown in the following description is added to eliminate the need for adjustment of positioning of the LEDs and adjustment of LED drive current for getting a uniform performance ratio to cope with variation in light emission characteristics of LEDs and to maintain ratio of intensity of light emission from the source A 11 to that from the source B 12 against large fluctuation in conditions of the surrounding environment with simple construction without fail, even when the device of the present invention is used in a vending machine which may be set-up in the outdoors.

In this circuit a comparator 27, a low-pass filter 28 and an adjustment circuit 29 are arranged to conduct adjustment of the intensity of light emission from the source B 12 to attain adjustment of the ratio of intensity of light emission from the source A 11 to that from B 12.

The comparator 27 compares voltage of output signal of the amplifier 26 with the reference voltage V1 to automatically adjust light emission of the source B 12 so as to equalize the output signal of photoelectric transducer 15 corresponding with quantity of the received light from the source A 11 with that from B 12, when there is no object to be identified, for example, a bank note between the sources A11, B 12 and the photoelectric transducer 15. The comparator 27 generates 0 V, if, for example, the output voltage of the amplifier 26 is higher than the reference voltage V1, and generates a specified voltage as it comes to a saturated state, if the output voltage of the amplifier 26 is lower than V1.

The low-pass filter 28 eliminates the alternating current component in the output of the comparator 27 and feeds the resulting signal to the adjustment circuit 29. Namely, the output voltage of the low-pass filter 28 shifts to a lower level than the present level, if the output from the comparator 27 is 0 V, while it moves toward a higher level than the present level, if the output from the comparator 27 is in the saturated state. It comes to be stabilized finally at a certain voltage level.

When a circuit 35 for detecting an object to be identified indicates that no object is detected, if the output signal of the low-pass filter 28 shifts to a lower voltage, it indicates that the intensity of light emission from the source A 11 is found to be higher than that from B 12 in comparison of light from A 11 with that from B 12 looking from the photoelectric transducer 15 and then the adjustment circuit 29 controls the control signal B so as to enhance light emission of the source B 12 by increasing the drive current from the source B drive circuit 3.

On the other hand, if the output signal of the low-pass filter 28 shifts to a higher voltage, it indicates that the intensity of light emission from the source B 12 is found to be higher than that from A 11 in comparison of light emission from A 11 with that from B 12, looking from the photoelectric transducer 15 and then the adjustment circuit 29 controls the control signal B so as to reduce light emission of the source B 12 by decreasing the drive current from the source B drive circuit 3. The aforementioned control process is repeated until the output voltage of the amplifier 26 is equalized with the reference voltage V1. By controlling as described above, it is possible to conduct automatic control so as to equalize the detected signal output of photoelectric transducer 15 corresponding with light emission from the source A 11 with that from the source B 12. As a result, any error in positioning the sources A 11 and B 12 or any variation in standards and specification of the light sources can be automatically eliminated. Further, any influence caused by deterioration of the light source due to aging or any variation in the performance of the light source or the photoelectric transducer 15 due to environmental change can be automatically eliminated.

This makes it unnecessary to conduct cumbersome adjustment works as required in the past to enable to cope with the fluctuation of set-up environment without any adjustment.

The adjustment circuit 29 conducts the above control and works to maintain the state of the control signal B at the time just before output of signal indicating detection of an object to be identified and stops adjustment based on the output signal from the low-pass filter 28, when such signal is generated from the circuit 35 for detecting the object to be identified. When generation of the signal indicating detection of an object to be identified is stopped from the circuit 35 for detecting the object to be identified, the adjustment circuit 29 resumes the above control process to control the control signal B so as to stabilize the voltage of the output signal of the low-pass filter 28 at a certain voltage.

It is not necessarily required to keep doing the above mentioned adjustment at all times, when there is no object to be identified and control may be started by activating the light sources with signals set before generation of the signal indicating detection of an object to be identified. Or else, the control signal B may be maintained within an acceptable range by activating the light sources once in every specified time interval to conduct control so as to extend life of the light sources by preventing exhaustion of the light source during time of waiting for the object to be identified.

The circuit 35 for detecting the object to be identified generates the signal indicating detection of an object to be identified to feed it to the adjustment circuit 29 indicating that an object 50 to be identified such as a bank note is transported to the location in the transportation path where the sources 11 or 12 and photoelectric transducer 15 are positioned, while either a sensor 36 or 37 for detecting an object to be identified is detecting transportation of an object to be identified.

The sensor 36 for detecting an object to be identified is, for example, disposed at a upstream position adjacent to the sources 11 and 12 in the transportation path of an object to be identified and the sensor 37 for detecting an object to be identified is disposed at a downstream position adjacent to the sources 11 and 12 in the transportation path of an object to be identified.

Shown in FIG. 2 is an example of circuit construction of the above described circuit for automatic adjustment of intensity of light emission of the light source.

In FIG. 2, a comparator 27*a* consisting of the comparator circuit 27 generates 0 V when voltage of the output 116 from the amplifier 26 is higher than the reference voltage V1, while it comes to saturation, when it is lower than V1.

In the circuit of FIG. 2, control of control suspension of the control signal B at the time of output of the signal indicating detection of an object to be identified from the circuit 35 for detecting an object to be identified is conducted by an analog switching circuit which is integrated with a low-pass filter part. The voltage of output signal of the low-pass filter part at the time when no output of the signal indicating detection of an object to be identified is generated from the circuit 35 for detecting an object to be identified shifts to a lower level than the present level, if the output of the comparator 27*a* is 0 V and to a higher level, if it is in a saturated state. It comes to final stabilization at a certain voltage.

A sample and hold part works simply as a buffer when no object to be identified is found and the low-pass filter output indicating no object found is generated as the control signal B. As a result, if it shifts to a lower voltage, the source B 12 drive current is increased as the source A 11 intensity is higher and if it shifts to a higher voltage, the source B 12 drive current is decreased as the source B 12 intensity is higher.

FIGS. 3A and 3B show an example of arrangements of the source A 11, B 12, the photoelectric transducer 15 and the sensors 36 and 37 for detecting an object to be identified shown in FIG. 1.

In FIG. 3A an object to be identified is transported in a direction perpendicular to the surface of the drawing and in FIG. 3B it is transported from the left-hand side of the drawing to the right-hand side. As shown in FIGS. 3A and 3B, the sources A 11 and B 12 are disposed with a specified distance between them, both of their light emission surfaces being directed toward the photoelectric transducer 15 so as to make the maximum quantity of their light emission reach to the photoelectric transducer 15.

Sensors 36 and 37 are disposed in the upstream side and downstream side, respectively, along the transportation path of the object 50 to be identified adjacent to the range of reach of the lights emitted from the sources A 11 and B 12 to the photoelectric transducer 15, so as to enable the sensors to detect arrival of the object to be identified at the detection range, when it is carried to the detection range either from the upstream side or the downstream side.

In FIG. 3*a* color filter 40*a* is disposed between the sources A 11, B 12 and the photoelectric transducer 15, if required, for adjusting wavelength of light which can be detected with better sensitivity corresponding with color of an object to be identified. This provides for an adjustment to sensitivity to a certain color, if color of a bank note to be identified is inclined toward a certain color. The color filter may be disposed either between the light sources and the object to be identified (40*a*) or between the object to be identified and the photoelectric transducer 15 (shown as 40*b* in FIG. 3A and 40 in FIG. 3B).

In this embodiment of the present invention, the direction shown in FIG. 3B is selected as one with the least off-set of light impinging on the object to be identified from the sources 11 and 12. This arrangement, of course, may be made as optional.

Now, the way of control for identification of the object to be identified in this embodiment of the present invention with the above construction is described. In this embodiment of the present invention, the detection output 116 is controlled so as to make it equal as the reference voltage V1 and the logarithmic amplifier output is controlled at a certain voltage level, before the object to be identified reaches within the detection range.

When the object to be identified arrives at the detection range under such a controlled state as the quantity of light emission from the sources A 11 and B 12 is fixed, the photoelectric transducer 15 generates electric signal corresponding with wavelength of emitted light from the sources 11 and 12 or wavelength through the color filter transmitted through the object to be identified. It, then, is amplified in the logarithmic amplifier 21 and is fed to the high-pass filter 22.

Suppose, for example, the light source A 11 is a red LED, while B 12 a green LED. In this case, the detected signal has a higher output voltage value at a timing of the source A emission than at a timing of the source B emission, if the color of the object to be identified in the detection range is more inclined to red than green or intensity of transmitted light from the source A 11 is higher than that from B 12. To the contrary, the detected signal has a higher output voltage value at a timing of the source B emission than that at a timing of the source A emission, if the color of the object to be identified in the detection range is more inclined to green than red or intensity of transmitted light from the source B 12 is higher than that from A 11.

The example shown in the left-hand side in the timing chart of FIG. 4 indicates a case in which detected signal has higher output voltage value at a timing of the source A emission than at a timing of the source B emission, with the color of the object to be identified in the detection range being more inclined to red than green, while the right-hand side of FIG. 4 indicates a case in which detected signal has higher output voltage value at a timing of the source B emission than at a timing of the source A emission, with the color of the object to be identified in the detection range being more inclined to green than red.

The high-pass filter 22 eliminates less-than-f components in the detected signal to extract alternating current component higher than f. Then the signal is superposed with the reference voltage V1 in the amplifier 23 for sampling, in the sampling circuit 24, the wave form data in the superposed wave form at the timing of detection of light emission from the source A 11 to hold it until the next sampling timing.

In this embodiment of the present invention, since the amplifier 23 generates output signal which fluctuates either to the positive side of the reference voltage V1 or to the negative side thereof in proportion to the variation of quantity of detected lights from the sources A 11 and B 12 or the difference between the detected signals of the photoelectric transducer when it receives the lights from both of the light sources, it is possible to detect to what extent the color of the object to be identified is inclined to red (when it swings to the positive side) or to what extent it is inclined to green (when it swings to the negative side) by only sampling detected signal at the timing of detecting light emission from the source A 11.

As a result there is no need to conduct color-by-color identification for a plurality of colors in the true-or-false identification process for a bank note described later. This enables to simplify construction in a large measure as it is possible to determine to what color the object to be identified is inclined out of a plurality of colors by simply checking only one kind of detected signal.

Then, the signal level of the result of sampling in the sampling circuit 24, which is the difference of the detected signal or difference of the color tint at the time of receipt of lights emitted from both of the sources A 11 and B 12 by the photoelectric transducer 15, is amplified to be fed to an identification part 30. As shown in FIG. 4 the color inclination of the object to be identified against the lights emitted from both of the source 11 and 12 is generated as one signal.

Accordingly, the identification part 30 following the amplifier 26 compares an output pattern in the output signal 116 by slicing it in a specified time frame with a reference pattern stored in the reference pattern storing part 31 which is to be obtained when a genuine bank note is detected to determine the degree of similarity. The object to be identified is determined to be genuine, if similarity is found not to be in excess of a specified degree.

As for such reference patterns, only one reference pattern is necessary to be stored for comparison for each bank note to be identified, enabling the identification process simpler. On top of that, it can aptly cope with errors of almost all colors, as it can handle errors of a plurality of colors, even though comparison with only one reference pattern is implemented.

As a result, it is possible to distinguish properly the genuine from the false, even when the object to be identified has only one side of a bank note printed on both sides or a double sided copy or single sided copy made by a duplicator.

The above mentioned light sources A 11 and B 12 are not necessarily limited to independent discrete LEDs but they may be integrated into a 2-colored LED. Such a construction will serve to simplify design by reducing mounting of an LED in only one location.

Figure 5:
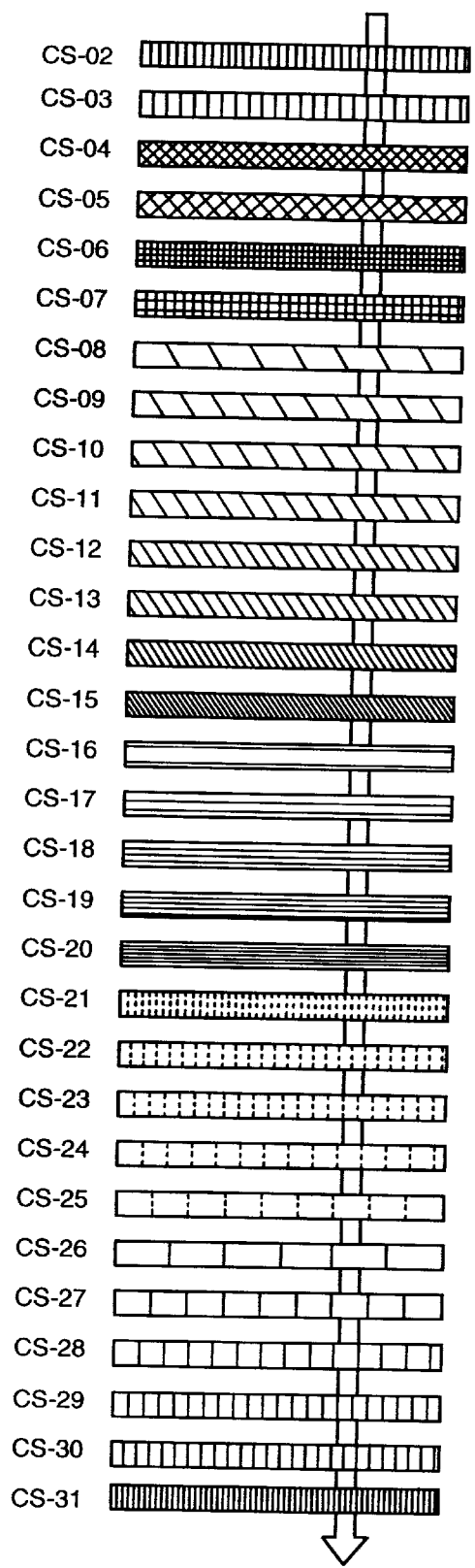
FIG. 5 is a drawing illustrating a color chart sample and relative direction of movement of identification position.
Figure 6:
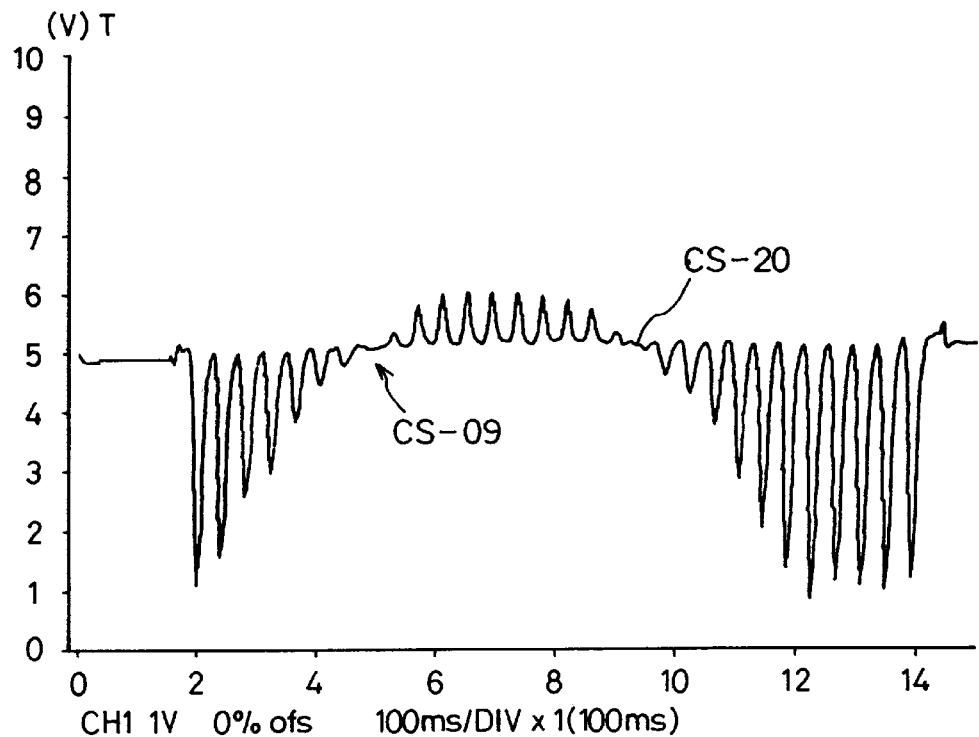
FIG. 6 is a graphic presentation illustrating an example of result of reading-out of a color chart sample according to an embodiment of the present invention.
Figure 7:
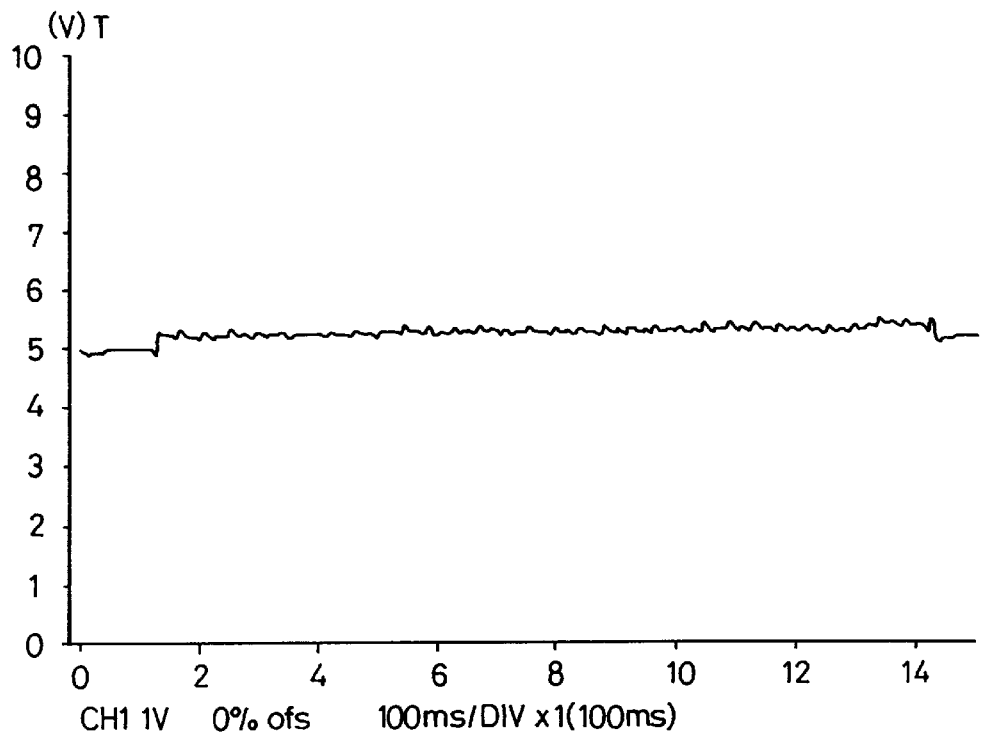
FIG. 7 is a graphic presentation illustrating the result of reading-out of a monochrome copy of the color chart sample according to an embodiment of the present invention.

An example of detection using an actual color chart with the construction shown in FIG. 1 is described in FIGS. 5 to 7.

The following reading-out was conducted by means of a construction using a 2-colored LED integrating red and green LEDs in one piece. In this example, a 2-colored LED is disposed so as to arrange 2 LED chips, each red and green, side by side to form a right angle to the line of transportation with the red diode chip working as the source B in the construction of FIG. 1.

A color chart sample of FIG. 5 is transported between the sources 11, 12 and the photoelectric transducer 15 at a speed of some 160 mm/sec. FIG. 5 shows the color chart only in luminance or in monochrome.

FIG. 6 illustrates graphically an example of the output signal 116 of the amplifier 26 with the reference voltage V1 being set at 5 v in the construction of FIG. 1.

As illustrated in FIG. 6 colors with the hues of red, orange, yellow and purple show swings toward lower levels than the reference voltage, while those with the hues of green and blue toward higher levels. This shows that there is a certain rate for each color in level of output value. As a result, when bank notes of a same kind in different conditions are read out, the variations in wave forms based on the reference voltage V1 for each of the bank notes in different conditions falls within a certain range, if we compare the wave forms for each bank note in different condition based on the reference voltage V1, even though bank notes of the same kind in different conditions show different output signals in the detection stage at the photoelectric transducer 15.

Accordingly, it is possible to attain a high degree of identification of genuine or false by comparing the wave form of an actual read-out signal based on the reference voltage V1 with a stored pattern, if a representative pattern of detected wave form for a certain kind of bank note is stored in advance as a reference.

FIG. 7 illustrates an example of output 116 obtained by transporting, in a similar way, a monochrome sample copy which was made by monochromatically copying of the color chart sample of FIG. 5 with a duplicator.

As shown in FIG. 7, the output 116 does not indicate much fluctuation, when there is only differences in lightness with no variation of chroma. Needless to compare with the wave form of FIG. 6, it takes quite a different wave form which makes it very easy to separate the false from the genuine.

As described above, it is possible to provide a device which is highly reliable and easy to manufacture and adjust and capable to automatically solve problems such as variations of performance of each component of the mechanism for detecting an object to be identified, change due to aging and change in performance due to surrounding environment with simple construction.

It is also enabled to conduct reliable identification of genuine or false with a simple algorithm, since it can express color difference between a genuine one and an object to be identified by one output signal in the detection result of the object to be identified.

Second Embodiment

The above description is made for an example in which the lights transmitted through an object to be identified from the light sources are detected by means of a photoelectric transducer 15. The present invention is, however, not limited to the above case but also may be applied to a case in which the lights emitted from the sources are reflected through an object to be identified so as to detect the reflected lights by means of a photoelectric transducer 15. A second embodiment of the present invention which is constructed as above is described below referring to FIGS. 8A and 8B. The second embodiment has a similar basic construction as the first embodiment shown in FIG. 1 described above but arrangements of the sources A 11, B 12 and the photoelectric transducer 15 are different. Those parts of the second embodiment different from the first embodiment are described below.

Figure 8A:
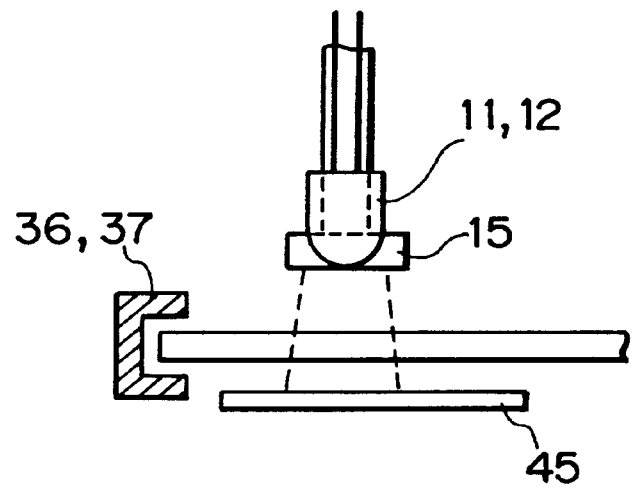
FIGS. 8A and 8B are drawings illustrating arrangement of the light emitting elements and the light receiving element in the second embodiment of the present invention.
Figure 8B:
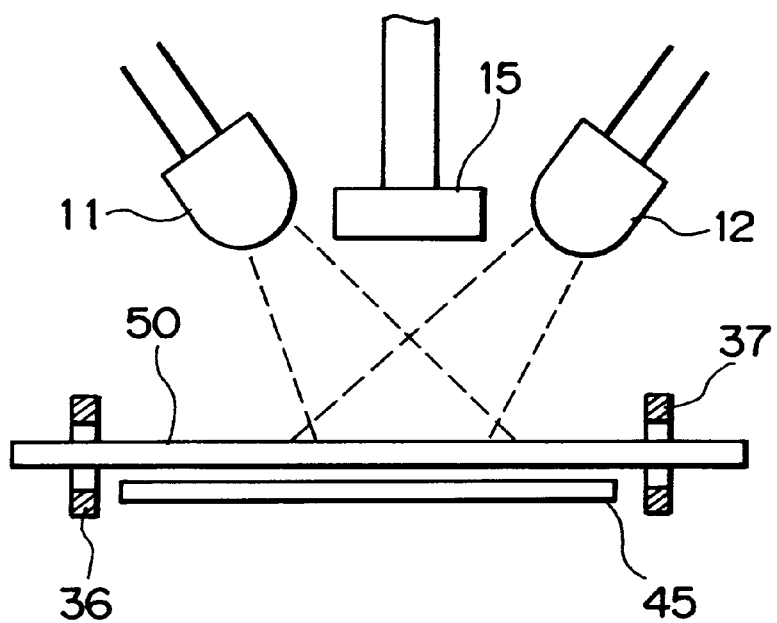

FIGS. 8A and 8B illustrate arrangements of the sources A 11, B 12, the photoelectric transducer 15, sensors 36 and 37 for detecting an object to be identified in the second embodiment of the present invention. In FIG. 8A an object to be identified is transported in a direction perpendicular to the surface of the drawing and in FIG. 8B it is transported from the left-hand side of the drawing to the right-hand side. As shown in FIGS. 8A and 8B, in the second embodiment of the present invention, the sources A 11 and B 12 are disposed so as to sandwich the photoelectric transducer 15. A reflector 45 for reflecting the lights emitted from the sources A 11 and B 12 is disposed under the transportation path of the object 50 to be identified.

The mounting positions of the sources A 11 and B 12 may be determined so as to make the reflected lights from the reflector 45 impinge on the photoelectric transducer 15. Such construction allows disposition of the light sources and the photoelectric transducer in adjacent locations to form an integrated optical system and to make the whole system in a compact size. Also, it is easy to make the reflector with a function of a color filter which can reflect a certain color more or less.

Other Embodiment

In the above descriptions, examples are shown in which red and green LEDs are used for the light sources. However, the present invention is not limited to the above examples but it can be applied to other embodiments which use light emitting devices with various wavelengths as long as two light sources have different wavelengths. For example, a combination of a red LED and a (green+infrared) LED or a combination of a red LED and infrared LED may be employed and it is sufficient to use a combination of two kinds of LEDs and not necessarily restricted by wavelengths. Also, it is not required to form two light sources by employing separate LEDs but rather they can be integrated in a two-colored LED as the example of reading-out of a sample stated above.

The duty factor of the drive pulse of the light source is set at 50% in the description but it is not necessarily limited to 50% but also any duty factor may be employed.

In the above description, described is a case in which analog signals are used for the output signals to the circuit for controlling light emission of the source B 12 encircled by a broken line in FIG. 1 and to the identification circuit 30. However, the present invention is not limited to the embodiment in which a signal is processed in analog but it may be applied to cases in which a signal is processed in digital by analog-to-digital conversion. In such cases, the output signal of the sampling circuit 24 is converted in an analog-to-digital conversion circuit to a digital signal corresponding with the analog signal to send it to the identification circuit 30 in which the detected digital signal is compared with the reference pattern stored as a digital signal in the reference pattern storing part 31 for digital pattern matching.

Figure 9:
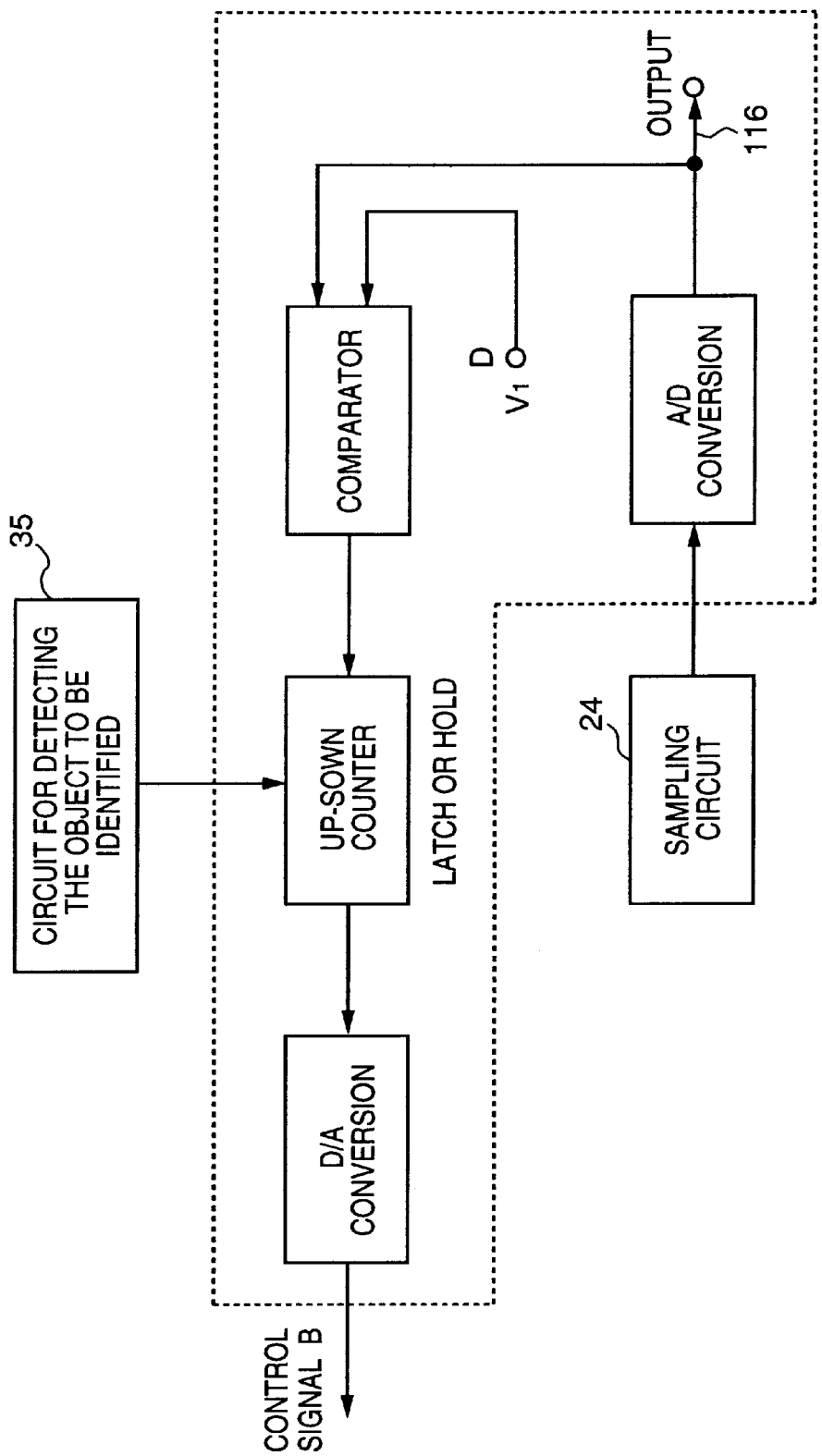
FIG. 9 is a block diagram illustrating detailed construction of the circuit surrounded by broken lines in FIG. 1 in another embodiment of the present invention.

In this case, the comparator 27 in the circuit for controlling light emission of the source B 12 compares the detected digital signal value with a digital reference value corresponding with the reference signal V1 to make the difference of two digital signals as up-count pulse or down-count pulse of an up-down counter. The count value of the up-down counter may be used as the control signal B by digital-to-analog conversion. When the part 35 for detecting an object to be identified generates a signal to indicate detection of an object to be identified, count value of the up-down counter may be kept in a hold-state. FIG. 9 shows an embodiment of such construction.

Various modifications and alterations of the present invention may be constructed without departing from the spirit and scope of the invention. It should be understood that the present invention is not limited to the specific embodiments described in this specification. To the contrary, the present invention is intended to cover various modifications and equivalent arrangements included within the spirit and scope of the claims.

What is claimed is:

1. A device for identifying a bank note comprising:
   first light emitting means for emitting light of a first wavelength;
   second light emitting means for emitting light of a second wavelength different from the first wavelength;
   first drive means for driving said first light emitting means to emit light;
   second drive means for driving said second light emitting means to emit light;
   light emission control means for activating said first and second drive means by alternately switching them;
   light receiving means for receiving light emitted by said first and second light emitting means and outputting electrical signals corresponding with intensities of received light;
   adjustment means for adjusting intensity of light by controlling at least one of said first and second drive means so that a difference in level between electrical signals corresponding with the light of the first and second wavelength and output by said light receiving means falls within a specified range;
   means for fixing the intensity of light to be emitted by said first and second light emitting means adjusted by said adjusting means when an object to be identified reaches a position between said first and second light emitting means and said light receiving means;
   extracting means for extracting an alternating current component of the electrical signals output from said light receiving means when said object to be identified is transported between said first and second light emitting means and said light receiving means; and
   sampling means for sampling the alternating current component extracted by said extracting means and emitted by one of said first and second light emitting means, whereby identification of the object is conducted based on a sampling value obtained by said sampling means.

2. A device for identifying a bank note as set forth in claim 1, wherein said identification of a bank note is conducted by checking similarity between the sampling value obtained from said sampling means and a value of a genuine object to be identified which is stored in advance.

3. A device for identifying a bank note as set forth in claim 1, wherein said first and second light emitting means are constructed with first and second LEDs, respectively, and said first and second LEDs and said light receiving means are arranged to face each other opposedly, said object to be identified being transported between said first and second LEDs and said light receiving means, while an optical filter is disposed between said first and second LEDs and said light receiving means.

4. A device for identifying a bank note as set forth in claim 3, wherein said first and second LEDs are constructed with a red LED and a green LED.

5. A device for identifying a bank note as set forth in claim 1, wherein said first and second light emitting means are constructed with first and second LEDs, respectively, and said light receiving means is disposed between said first and said second LEDs so as to be able to receive light emitted from both of said first and second LEDs after the light is reflected from a reference reflector, while said object to be identified is transported between said first LED, said second LED, said light receiving means and said reference reflector.

6. A device for identifying a bank note as set forth in claim 5, wherein said first and second light emitting diodes are constructed with a red LED and a green LED.

7. A device for identifying a bank note as set forth in claim 3, wherein said first and second light emitting diodes are integrated into a 2-colored LED.

8. A device for identifying a bank note as set forth in claim 5, wherein said first and second light emitting diodes are integrated into a 2-colored LED.

9. A method for identifying a bank note with a device including 2 kinds of light emitting means emitting light in different wavelengths, and light receiving means for outputting electrical signals corresponding with detected light intensity by receiving light emitted from said 2 kinds of light emitting means, said method comprising the steps of;

controlling the intensity of light emission from said 2 kinds of light emitting means so as to equalize approximately the electrical signals from said 2 kinds of light receiving means by sequentially switching said 2 kinds of light emitting means, when said object to be identified is not being identified, to eliminate variations in performance of both of said 2 kinds of light emitting means and said light receiving means;

emitting light from said 2 kinds of light emitting means at an intensity of light emission controlled before identification, when said object to be identified is being identified;

extracting an alternating current component in an output of said light receiving means to determine variations of quantity of received light from said 2 kinds of said light emitting means when said object to be identified is transported between both of said 2 kinds of light emitting means and said light receiving means;

detecting variations in the output of said light receiving means as derived from received light from one of said 2 kinds of light emitting means; and identifying a bank note as a genuine one by determining that the detected variations are similar to a pattern stored in advance.

* * * * *